United States Patent
Neilan et al.

(10) Patent No.: US 12,115,288 B2
(45) Date of Patent: *Oct. 15, 2024

(54) COATED MEDICAL DEVICE AND METHOD OF COATING SUCH A DEVICE

(71) Applicant: Cook Medical Technologies LLC, Bloomington, IN (US)

(72) Inventors: John Neilan, Gort (IE); David Murray, Limerick (IE); James Butler, Aherlow (IE)

(73) Assignee: Cook Medical Technologies LLC, Bloomington, IN (US)

( * ) Notice: Subject to any disclaimer, the term of this patent is extended or adjusted under 35 U.S.C. 154(b) by 842 days.

This patent is subject to a terminal disclaimer.

(21) Appl. No.: 16/510,352

(22) Filed: Jul. 12, 2019

(65) Prior Publication Data

US 2020/0016299 A1    Jan. 16, 2020

Related U.S. Application Data

(63) Continuation-in-part of application No. 16/033,765, filed on Jul. 12, 2018, now Pat. No. 10,874,772.

(30) Foreign Application Priority Data

Jul. 12, 2018    (GB) .................................... 1811439

(51) Int. Cl.
| | |
|---|---|
| A61L 31/08 | (2006.01) |
| A61F 2/90 | (2013.01) |
| A61L 27/28 | (2006.01) |
| A61L 27/54 | (2006.01) |
| A61L 31/16 | (2006.01) |

(52) U.S. Cl.
CPC ............... *A61L 31/08* (2013.01); *A61F 2/90* (2013.01); *A61L 27/54* (2013.01); *A61L 31/16* (2013.01); *A61F 2250/0067* (2013.01); *A61L 27/28* (2013.01); *A61L 2300/416* (2013.01); *A61L 2420/02* (2013.01)

(58) Field of Classification Search
None
See application file for complete search history.

(56) References Cited

U.S. PATENT DOCUMENTS

| | | | | |
|---|---|---|---|---|
| 5,372,660 | A * | 12/1994 | Davidson | A61L 31/022 623/923 |
| 7,056,591 | B1 * | 6/2006 | Pacetti | A61L 31/10 623/1.49 |
| 2003/0077310 | A1 * | 4/2003 | Pathak | A61L 31/125 604/500 |
| 2005/0287184 | A1 * | 12/2005 | Hossainy | A61L 31/16 514/171 |
| 2006/0062825 | A1 * | 3/2006 | Maccecchini | A61K 38/18 427/2.26 |
| 2007/0043423 | A1 * | 2/2007 | Grewe | A61F 2/885 623/1.42 |
| 2007/0077440 | A1 * | 4/2007 | Gawalt | A61L 29/106 428/469 |
| 2008/0038307 | A1 * | 2/2008 | Hoffmann | A61P 43/00 523/121 |
| 2008/0183278 | A1 * | 7/2008 | Atanasoska | A61F 2/82 623/1.42 |
| 2008/0241218 | A1 * | 10/2008 | McMorrow | A61P 7/00 424/426 |
| 2008/0306591 | A1 * | 12/2008 | Wang | A61L 31/10 528/354 |
| 2009/0005856 | A1 * | 1/2009 | Pappas | A61F 2/915 623/1.16 |
| 2011/0206754 | A1 * | 8/2011 | Morra | A61P 29/00 606/301 |
| 2011/0238163 | A1 * | 9/2011 | Andrews | A61L 29/14 526/318.4 |
| 2011/0276124 | A1 * | 11/2011 | Doerr | A61L 27/52 623/1.15 |
| 2015/0190555 | A1 * | 7/2015 | Mani | A61L 31/16 623/1.42 |
| 2016/0067069 | A1 * | 3/2016 | Yamauchi | C22C 19/007 148/563 |
| 2018/0280584 | A1 * | 10/2018 | Zhang | A61L 31/10 |

FOREIGN PATENT DOCUMENTS

WO    WO-2017117922 A1 *    7/2017    ............. A61B 17/68

OTHER PUBLICATIONS

Szklarska et al. Acta Physica Polonica A 2014 125(4):919-923 (Year: 2014).*
Sgorla et al. International Journal of Pharmaceutics 2016 511:380-389 (Year: 2016).*
Lih et al. Journal of Tissue Engineering 2016 7:1-11 (Year: 2016).*
Aoki et al. Cardiovascular Intervention and Therapeutics 2021 36:23-29 (Year: 2021).*
Thiruppathi et al. Langmuir 2015 31:358-370 (Year: 2015).*

* cited by examiner

Primary Examiner — Melissa S Mercier
Assistant Examiner — Caralynne E Helm
(74) Attorney, Agent, or Firm — Woodard, Emhardt, Henry, Reeves & Wagner, LLP

(57) ABSTRACT

A medical device such as a stent (10) or medical balloon (40) is at least partially coated with a saturated carboxylic acid layer in order to enhance biocompatibility, reduce thrombogenesis and increase endothelialisation. The coating is preferably of citric acid in non-crosslinked form and preferably non-porous so as to mask the underlying structure of the medical device. The acid coating forms an outer surface of at least a part of the medical device, that is has no other layer or material overlying it, save for in some embodiments a partial coating of a bioactive material.

19 Claims, 10 Drawing Sheets

COATED MEDICAL DEVICE AND METHOD OF COATING SUCH A DEVICE

CROSS REFERENCE TO RELATED APPLICATIONS

This application claims the benefit of Great Britain patent application No. 1811439.7 filed on Jul. 12, 2018, entitled "Coated Medical Device and Method of Coating Such a Device" and U.S. nonprovisional patent application Ser. No. 16/033,765 filed on Jul. 12, 2018 entitled "Coated Medical Device and Method of Coating Such a Device" the entire contents of which are incorporated herein by reference. European patent application No. 19186074.1 filed on Jul. 12, 2019, is a related application to the above mentioned.

TECHNICAL FIELD

The present invention relates to a coated medical device, particularly with improved biocompatibility, in the preferred embodiments with improved antithrombogenicity and/or improved endothelialisation characteristics. The invention can be used with implantable medical devices such as stents, stent grafts, vascular filters and plugs, valvuloplasty devices and so on. It can also be applied to medical devices intended to be deployed temporarily in a patient, such as angioplasty balloons, valvuloplasty balloons, medical device deployment balloons, introducer assembly components, pacemaker leads, vessel ablation devices and so on.

BACKGROUND OF THE INVENTION

Coated medical devices, particularly endoluminally deployable medical devices, are known for a variety of medical applications. Medical devices may be implanted in a patient long term or even permanently, or may be temporarily used, such as in the case of a treatment balloon, catheter, cannula, guide wire, ablation terminals and the like.

Implantable medical devices and medical apparatus, whether for long term or temporary placement, can cause significant side effects for a variety of causes, including as a result of being seen by the body as foreign objects. This can result in thrombus formation, reduced or suppressed endothelialisation and so on.

Thrombogenesis, or blood clot formation, experienced during the use of implanted medical devices or other medical apparatus, occurs as a result of a number of causes, including: the action of shear forces within the body, for instance on the vessel walls in which the device is deployed, the body's physiological reaction to the foreign body, surface roughness, surface energy, geometry and hydrophilicity of the exposed surfaces of the implantable medical device and so on. For instance, when blood-clotting proteins such as thrombin receive a signal that the blood is being sheared, a cascade of events is initiated to cause blood to clot in the vicinity of the event, in an effort to stop perceived bleeding. There are two primary forms of thrombosis pathways, intrinsic and extrinsic, each of which forms comprises multiple points or biochemical pathways that can trigger the clotting cascade. It is not just shear forces that may trigger a cascade, as explained above, with the result that there is a multitude of other cascades that can result in thrombogenesis, including the body's natural immune response. Medical implant induced thrombogenesis can result in exaggerated healing responses, resulting in restenosis.

In order to mitigate these effects, medical device manufacturers have developed a variety of coatings to limit the possibility of clotting. Typical coatings are designed to elute, over a period of time, an antithrombogenic agent from a carrier matrix. Heparin and heparin sulphate are well known antithrombogenic agents, while a variety of carrier agents are also known, a porous polymer being one of many known examples. A problem with such coatings is that their effect is time limited, often relatively short term, and can also suffer from poor biocompatibility of the carrier matrix, leading to further physiological complications.

Another issue with the use of implantable medical devices lies with their effect on endothelialisation.

The endothelium is a single layer of endothelium cells that lines the vascular walls and plays an integral part in maintaining homeostasis. The implantation of medical devices, whether temporary or long term, can cause significant injury to the vascular wall and endothelium, leading to inflammation, triggering of repair mechanisms and the formation of neointimal hyperplasia. The ability of the endothelium to repair itself depends both on the migration of surrounding mature endothelial cells and the attraction and adhesion of circulating endothelial progenitor cells (EPCs) to the injured region, which then differentiate into endothelial-like cells. When the vessel is subject to the implantation of a permanent or temporary foreign object such as a medical device, there is a high risk of thrombosis as a result of the foreign surfaces introduced into the patient. If or when the implanted device gets covered in endothelial cells, the risk of thrombosis is greatly reduced.

Current therapies, such as drug-eluting stents, interrupt this natural response to healing, often as a result of the cytotoxic nature of the drug. As a consequence, the vascular wall is unable to heal optimally and the medical device remains exposed in the vessel for longer than ideal.

While there are materials and bioactive compounds that have advantageous thrombogenic or endothelialisation properties, such as some polymers and hyperbalanced polyglycerol (HPG), these are considered not to be suitable for the manufacture of many medical devices or for coating such devices, as they either do not exhibit optimum mechanical properties or can lead to an increase in the dimensions or footprint of the devices.

The teachings herein are intended to address one or more of the problems identified above.

Some examples of known medical device surface treatments are disclosed in US-2011/0093057, US-2013/0045277, U.S. Pat. Nos. 8,404,264, 9,211,363, the article by Inoue et al in the Wiley Online Library published on 22 Dec. 2012 entitled "Poly-(L-lactic acid) and citric acid-cross-linked gelatin composite matrices as a drug-eluting stent coating material with endothelialisation, antithrombogenic, and drug release properties", and the article by Hirofumi Saito in Biomacromolecules 2007, 8, 1992-1998 entitled "Unusual Cell Adhesion and Antithrombogenic Behaviour of Citric Acid-Cross-Linked Collagen Matrices".

SUMMARY OF THE INVENTION

The present invention seeks to provide an improved coated medical device, method of preparing and coating such a device, and treatment of a medical device to reduce or eliminate thrombosis caused by the medical device and/or to improve endothelialisation following deployment or implantation of a medical device.

According to an aspect of the present invention, there is provided a medical device including:

a structure for implantation or disposition inside a patient, the structure including at least one surface;

wherein the at least one surface is at least partially covered by a layer of a saturated carboxylic acid or a derivative or carboxylic acid;

said layer being an outermost layer of the structure.

The outermost layer may be for enhancing endothelialisation. The acid of the layer is preferably not polymerised. The acid of the layer may be monomeric.

The layer of saturated carboxylic acid (or derivative thereof), it has been found, provides good biocompatibility and is able to mask the underlying structure of the medical device from the body, effective in reducing or suppressing disadvantageous effects experienced in the implantation of medical devices into a patient. In other words, the medical device is provided with a coating of a saturated carboxylic acid as an outermost layer of the device or a part of the device. This acts as a mask to promote endothelialisation and/or reduce thrombosis. The carboxylic acid outer coating or layer comes into direct contact with the vessel wall tissue or endothelium and/or with the blood plasma.

The carboxylic acid may be a saturated carboxylic acid or an unsaturated carboxylic acid. Preferably the carboxylic acid is a saturated carboxylic acid. Saturated carboxylic acids include for example, citric acid, hyaluronic acid, formic acid, acetic acid, oxalic acid, glyoxylic acid and glycolic acid.

Preferably, the layer of a saturated carboxylic acid or derivative thereof is a non-porous layer. In other words, the layer does not act as a matrix or absorb other compounds, such as bioactive agents, any components of blood plasma or the like. A non-porous layer has the effect of providing an effective mask over the at least one surface. On the other hand, the layer of saturated carboxylic acid or derivative thereof can act as a surface to which endothelial cells will readily adhere.

The layer is preferably at least 90% saturated carboxylic acid or derivative thereof, most preferably is exclusively, that is consists of a saturated carboxylic acid or derivative thereof. The layer is preferably made of pure saturated carboxylic acid. The skilled person will appreciate that when a layer is described as being exclusively of or consisting of or purely of a material that there may be trace amounts of other materials, such as remnants of a carrier (e.g. solvent), and other impurities, but that these have no material effect on the characteristics of the main constituent, that is of the saturated carboxylic acid or derivative thereof.

Advantageously, the layer is carrier free. Advantageously the layer is free of one or more of a) containment elements; b) binding agents; c) time control release agents; d) polymer and e) other matrix materials.

The preferred embodiment has a layer of citric acid. This has been found particularly effective for the described uses and effects, particularly because citric acid is not perceived by the body as a foreign material. The inventors have found that this can provide a very effective mask over one or more surfaces of a medical device, as explained in further detail below.

The layer is preferably formed of saturated amorphous carboxylic acid or derivative thereof, in the preferred embodiment of amorphous citric acid. In some embodiments the outermost layer may be crystalline.

Advantageously, the layer is formed of non-crosslinked molecules in the preferred embodiment of non-crosslinked citric acid molecules.

Preferably, the layer covers at least 80% of the at least one surface, more preferably substantially 100% of the at least one surface.

In the preferred embodiments, the layer is as thin as possible. It is envisaged that this may be in the thickness of tens of Angstroms. In some embodiments, the layer may have a thickness of 10 nanometres to 200 nanometres, preferably of no more than 100 nanometres.

In a practical embodiment, the layer includes in the region of 100 micrograms of carboxylic acid or derivative thereof. This may be on a stent having a length of 40 mm.

In the case of a layer formed of or comprising citric acid, given that the molecular size of citric acid is: a-axis=about 1.1 nanometres (11 Å), b-axis is=about 0.6 nanometres (6 Å) and the c-axis=about 1.3 nanometres (13 Å), the layer can be only a few molecules in thickness and be effective.

In some embodiments, there may be provided an interstitial layer between the at least one surface and the outermost layer of a saturated carboxylic acid or derivative thereof.

In an example, the medical device includes an abluminal and a luminal surface, wherein at least one of the abluminal and luminal surfaces is covered by a layer of a saturated carboxylic acid or derivative thereof as an outermost layer of said at least one surface. For instance, one of the abluminal and luminal surfaces may be covered by a layer of a saturated carboxylic acid or derivative thereof as an outermost layer of said at least one surface and the other of the abluminal and luminal surfaces is covered by a layer of a carboxylic acid or derivative thereof underlying a layer of bioactive agent. Advantageously, the bioactive agent layer consists of or is principally of bioactive material, preferably a therapeutic substance, in the preferred embodiments paclitaxel, docetaxel, or derivatives thereof.

According to another aspect of the present invention, there is provided a use of a medical device including a structure for implantation or disposition inside a patient, the structure including at least one surface, wherein the at least one surface is covered by a layer of a saturated carboxylic acid or a derivative of saturated carboxylic acid, said layer being an outermost layer of the structure, in the reduction or prevention of thrombogenesis.

According to another aspect of the present invention, there is provided a use of a medical device including a structure for implantation or disposition inside a patient, the structure including at least one surface, wherein the at least one surface is covered by a layer of a carboxylic acid or a derivative of carboxylic acid, said layer being an outermost layer of the structure, in the enhancement of endothelialisation.

The application of the layer of a saturated carboxylic acid or derivative thereof could be described as functionalisation of the at least one surface of the structure by subjecting the at least one surface to acidification or basification. The functionalization causes an increase in acidic or basic polar components at the at least one surface.

In some embodiments, at least one surface of the medical device may have applied over the coating a layer of a bioactive material. The layer of bioactive material may: a) consist of or be principally of bioactive material; b) be or include a therapeutic substance; c) be or include an antiproliferative bioactive substance; and/or d) be or include paclitaxel.

Advantageously, the layer of bioactive material is free of one or more of: a) containment elements; b) binding agents; c) time control release agents; and d) polymer or other matrix material, all of which being of a type intended to slow the release of the bioactive agent when in the vessel to provide a time delayed administration of the bioactive agent into the patient. The bioactive agent may, on the other hand, be provided with an excipient intended to facilitate and/or accelerate the transfer of the bioactive agent once in situ in the patient. Urea is a known excipient for such purposes.

Preferably, the acidified or basified surface (that is the layer) is substantially impervious to the bioactive material.

Preferably, the entirety of the at least one surface is functionalised, that is provided with the layer of a saturated carboxylic acid or derivative thereof.

The preparation of the medical device may include the step of atomically cleaning the at least one surface prior to functionalisation (application of the layer of a saturated carboxylic acid or derivative thereof). Such cleaning can increase the uniformity of functionalisation of the surface.

Preferably, the at least one surface is atomically cleaned without removal of the oxide on the at least one surface. The at least one surface may be atomically cleaned by plasma cleaning, for example an $O_2$ $H_2$ plasma. Other suitable plasmas may be used, for example of purified water or of evaporated ethanol. In some embodiments, cleaning may be caustic cleaning, such as with NaOH.

The method may also include the step of cleaning the at least one surface with an alcohol prior to functionalization (application of the layer of a carboxylic acid or derivative thereof), in order to remove contaminants from the surface. Advantageously, the step of cleaning the at least one surface with alcohol is carried out prior to any atomic cleaning of the surface. Ethanol is a suitable cleaning agent for this step.

Acids used for functionalisation of the surface may have a range of acidities. A strong acid, of around 1.5 pH acidity, is particularly effective.

In a practical embodiment, the at least one surface may be coated by treatment with an acid for around five minutes. Treatment times may vary, for instance in dependence upon concentration of the acid, strength of the acid and so on.

In some embodiments, the at least one surface may be coated by treatment with citric acid, a combination of citric and acrylic acids, or derivatives thereof.

It is preferred that the at least one acidic component includes one or more of: O—C=O; C—O, C—OH; and C=O.

The at least one functionalised or coated surface may also include a dispersal facilitator, such as a C—C component.

The medical device may be of any of the varieties described above and elsewhere in this specification. Examples include stents and medical balloons, grafts, embolization coils, filters, occluders, embolization devices, prosthetic valves, catheters, cannulae, wire guides, diagnostic tools and so on. The medical device may be made of metal, for example a nickel titanium alloy. Where the medical device is a stent or has a similar support member or scaffold the medical device may be made of a metal or metal alloy, such as a nickel titanium alloy. The stent could equally be made of other materials known in the art.

Where the medical device is or includes a balloon, or otherwise would benefit from fast release of the bioactive material, the coating may include or overlie an excipient.

Other aspects and advantages of the teachings herein are described below in connection with the preferred embodiments disclosed herein.

BRIEF DESCRIPTION OF THE DRAWING

Embodiments of the present invention are described below, by way of example only, with reference to the accompanying drawings, in which.

DETAILED DESCRIPTION

Figure 1:
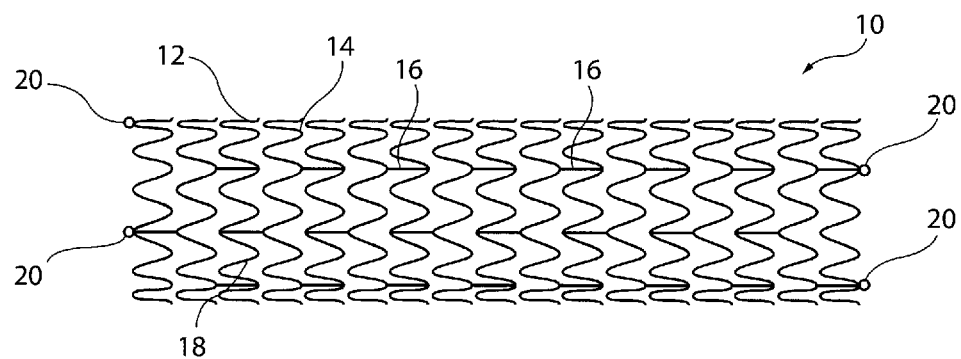
FIG. 1 is a side elevational view of an exemplary vascular stent.

It is to be understood that the drawings are schematic only and not to scale. Often only the principal components relevant to the teachings herein are shown in the drawings, for the sake of clarity.

The embodiments described below focus on a stent and medical balloon. It is to be understood, however, that these are examples only and that the teachings herein can be applied to a large range of medical devices, both for temporary placement in a patient and also for long term placement. Other examples include stent grafts, vascular filters and plugs, valvuloplasty devices, prostheses and so on.

The term "bioactive material" as used herein is intended to encompass any material or compound intended to provide a bioactive or therapeutic effect.

The invention contemplates the use of any one or combination of carboxylic acids, not just the preferred acids and derivatives disclosed in detail herein. Any one or more of the following carboxylic acids may be used: formic acid, acetic acid, oxalic acid, glyoxylic acid, glycolic acid, propionic acid, ethanecarboxylic acid, acrylic acid, acroleic acid, ethylenecarboxylic acid, propene acid, vinylformic acid, malonic acid, methanedicarboxylic acid, pyruvic acid, a-ketopropionic acid, acetylformic acid, pyroracemic acid, lactic acid, milk acid, butyric acid, propanecarboxylic acid, isobutyric acid, isobutanoic acid, succinic acid, acetoacetic acid, fumaric acid, trans-1,2-ethylenedicarboxylic acid, 2-butenedioic acid, trans-butenedioic acid, allomaleic acid, boletic acid, donitic acid, lichenic acid, maleic acid, cis-butenedioic acid, maleinic acid, toxilic acid, oxaloacetic acid, oxalacetic acid, oxosuccinic acid, malic acid, hydroxybutanedioic acid, tartaric acid, 2,3-dihydroxysuccinic acid, threaric acid, racemic acid, uvic acid, paratartaric acid, crotonic acid, trans-2-butenoic acid, beta-methylacrylic acid, 3-methylacrylic acid, (E)-2-butenoic acid, valeric acid, valerianic acid, butane-1-carboxylic acid, glutaric acid, propane-1,3-dicarboxylic acid, 1,3-propanedicarboxylic acid, n-pyrotartaric acid, alpha-Ketoglutaric acid, 2-ketoglutaric acid, α-ketoglutaric acid, 2-oxoglutaric acid, oxoglutaric acid, caproic acid, n-caproic acid, adipic acid, hexane-1,6-dioic acid, citric acid, 3-carboxy-3-hydroxypentanedioic acid, 2-hydroxy-1,2,3- propanetricarboxylic acid, aconitic acid, achilleic acid, equisetic acid, citridinic acid, pyrocitric acid, isocitric acid, sorbic acid, enanthic acid, oenanthic acid, n-Heptylic acid, n-Heptoic acid, pimelic acid, benzoic acid, carboxybenzene, dracylic acid, salicylic acid, caprylic acid, Phthalic acid, pelargonic acid, 1-octanecarboxylic acid, trimesic acid, cinnamic acid, trans-cinnamic acid, phenylacrylic acid, cinnamylic acid, 3-phenylacrylic acid, (E)-cinnamic acid, benzenepropenoic acid, isocinnamic acid, capric acid, decanoic acid, sebacic acid, 1,8-octanedicarboxylic acid, hendecanoic acid, lauric acid, dodecylic acid, dodecoic acid, laurostearic acid, fulvic acid, 1-undecanecarboxylic acid, duodecylic acid, mellitic acid, graphitic acid, benzenehexacarboxylic acid, tridecylic acid, myristic acid, pentadecylic acid, palmitic acid, margaric acid heptadecylic acid, stearic acid, oleic acid, (9Z)-octadecenoic acid, (Z)-octadec-9-enoic acid, cis-9-octadecenoic acid, cis-Δ9-octadecenoic acid, linoleic acid, ALA α-linolenic acid, cis, cis, cis-9,12,15-octadecatrienoic acid, (Z,Z,Z)-9,12,15-octadecatrienoic acid, GLA, γ-linolenic acid, gamolenic acid, SDA, stearidonic acid moroctic acid, nonadecylic acid, arachidic acid, eicosanoic acid, arachic acid, Mead's acid, AA, ARA, arachidonic acid, behenic acid, DHA, cervonic acid, tricosylic acid, lignoceric acid, pentacosylic acid, cerotic acid.

The carboxylic acids may be saturated or unsaturated. Saturated carboxylic acids may include formic acid, acetic acid, oxalic acid, hyaluronic acid, glyoxylic acid, propionic acid, ethanecarboxylic acid, malonic acid, methanedicarboxylic acid, pyruvic acid, α-ketopropionic acid, acetylformic acid, pyroracemic acid, lactic acid, milk acid, butyric acid, propanecarboxylic acid, isobutyric acid isobutanoic acid, succinic acid, acetoacetic acid, oxaloacetic acid, oxalacetic acid, oxosuccinic acid, malic acid, hydroxybutanedioic acid, tartaric acid, 2,3-dihydroxysuccinic acid, threaric acid, racemic acid, uvic acid, paratartaric acid, valeric acid, valerianic acid, butane-1-carboxylic acid, glutaric acid, propane-1,3-dicarboxylic acid, 1,3-propanedicarboxylic acid, n-pyrotartaric acid, alpha-Ketoglutaric acid, 2-ketoglutaric acid, α-ketoglutaric acid, 2-oxoglutaric acid, oxoglutaric acid, caproic acid, n-caproic acid, adipic acid, hexane-1,6-dioic acid, citric acid, 3-carboxy-3-hydroxypentanedioic acid, 2-hydroxy-1,2,3-propanetricarboxylic acid, isocitric acid, enanthic acid, oenanthic acid, n-Heptylic acid, n-Heptoic acid, pimelic acid, benzoic acid, carboxybenzene, dracylic acid, salicylic acid, caprylic acid, pelargonic acid, 1-octanecarboxylic acid, trimesic acid, capric acid, decanoic acid, sebacic acid, 1,8-octanedicarboxylic acid, hendecanoic acid, lauric acid, dodecylic acid, dodecoic acid, laurostearic acid, fulvic acid, 1-undecanecarboxylic acid, duodecylic acid, mellitic acid, graphitic acid, benzenehexacarboxylic acid, tridecylic acid, myristic acid, pentadecylic acid, palmitic acid, margaric acid, heptadecylic acid, stearic acid, ALA, arachidic acid, eicosanoic acid, arachic acid, behenic acid, tricosylic acid, lignoceric acid, pentacosylic acid and cerotic acid. Unsaturated carboxylic acids may include acrylic acid, acroleic acid, ethylenecarboxylic acid, propene acid, vinylformic acid, fumaric acid, trans-1,2-ethylenedicarboxylic acid, 2-butenedioic acid, trans-butenedioic acid, allomaleic acid, boletic acid, donitic acid, lichenic acid, maleic acid, cis-butenedioic acid, maleinic acid, toxilic acid, crotonic acid, trans-2-butenoic acid, beta-methylacrylic acid, 3-methylacrylic acid, (E)-2-butenoic acid, aconitic acid, achilleic acid, equisetic acid, citridinic acid, pyrocitric acid, sorbic acid, cinnamic acid, trans-cinnamic acid, phenylacrylic acid, cinnamylic acid, 3-phenylacrylic acid, (E)cinnamic acid, benzenepropenoic acid, isocinnamic acid, oleic acid, (9Z)-octadecenoic acid, (Z) -octadec-9-enoic acid, cis-9-octadecenoic acid, cis-Δ9-octadecenoic acid, linoleic acid, nonadecylic acid, Mead's acid, AA, ARA, arachidonic acid, DHA, cervonic acid, Phthalic acid, α-linolenic acid, cis, cis,cis-9,12,15-octadecatrienoic acid, (Z,Z,Z)-9,12,15-octadecatrienoic acid, GLA, γ-linolenic acid, gamolenic acid, SDA, stearidonic acid, and moroctic acid.

It is preferred to use saturated carboxylic acids that exist and most preferably are prevalent in the human body.

Referring first to FIG. 1, there is shown an exemplary vascular stent 10 to which the teachings herein can be applied. The stent 10 is generally a tubular structure 12, in this example formed of a plurality of stent rings 14 that extend in series coaxially along the length of the tubular structure 12 and are coupled to one another by means of tie bars 16, well known in the art. In this example, the stent rings 14 are formed of a plurality of strut sections 18 arranged a zigzag shape. At the end of the stent 10 there may be provided radiopaque markers 20, again of a type well known in the art.

The stent 10 may be self-expanding or balloon expandable and made of any suitable material, of which many are known in the art.

Figure 2:
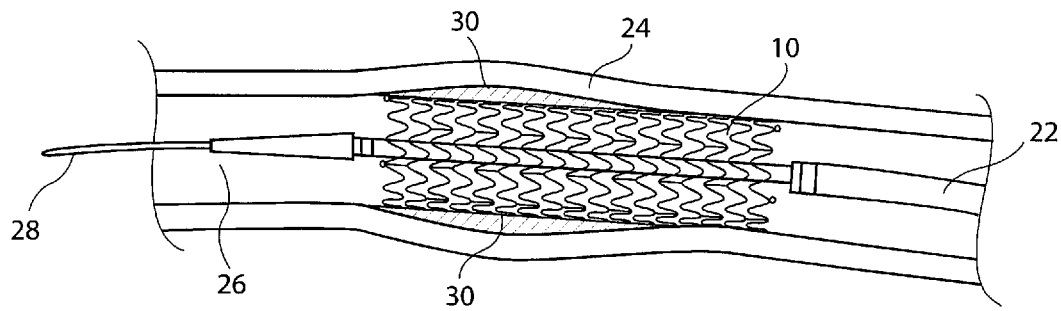
FIG. 2 is a schematic representation of the stent of FIG. 1 in the process of being deployed in a patient's vessel to treat a stenosis.

Referring also to FIG. 2, the stent 10 can be seen in the process of being deployed into a vessel 24, by means of an introducer assembly of which the distal end components 22 are visible in FIG. 2. These typically include a carrier element having a dilator tip 26 at the distal end thereof. The dilator tip 26 has a lumen therein for the passage of a guide wire 28. The components of the introducer assembly are not relevant to the teachings herein.

In the example in FIG. 2, the stent 10 is being deployed in order to treat a stenosis 30 of the vessel 24 and also to keep the vessel 24 open for the passage of blood therethrough.

Often, the deployment of a stent alone in the vessel does not provide a permanent solution as restenosis can often occur, closing the vessel again. This can be caused by a number of factors, including damage to the tissue of the vessel 24 during the vessel opening or angioplasty procedure, reoccurrence of the original causes of the stenosis, body reaction to the presence of a foreign body in the vessel, and so on.

Figure 3:
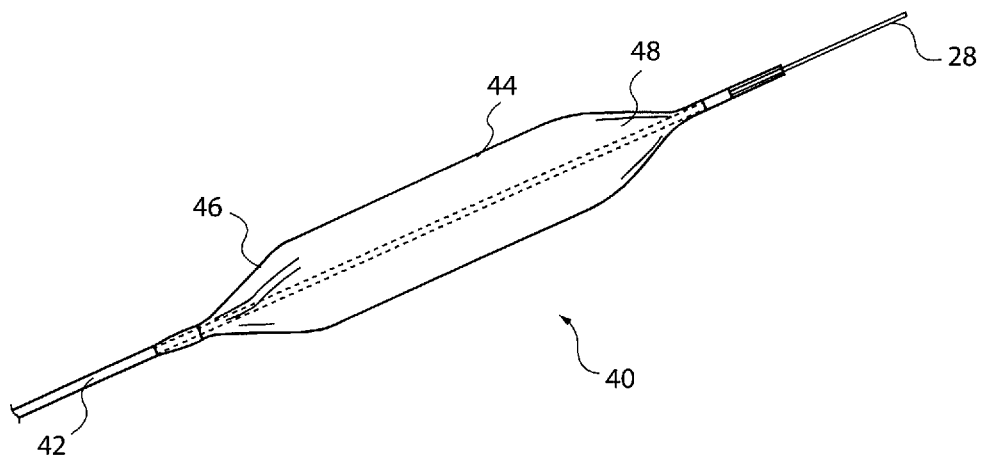
FIG. 3 is a side elevational view of an exemplary angioplasty balloon.

Referring now to FIG. 3, this shows an exemplary medical balloon 40 which may be used for angioplasty procedures, for deployment of a medical device such as a stent or stent graft, for valvuloplasty procedures or the like. The medial balloon is fitted to a balloon catheter 42 and has a substantially cylindrical balloon body 44 terminating in end cones 46, 48 which taper towards the balloon catheter 42 and fix the balloon wall to the catheter in fluid-tight manner. The balloon catheter 42 may include a lumen therein for the passage of a guide wire 28 as well as a lumen for providing inflation fluid into the balloon. The basic structure of the balloon 40 may be of a type conventional in the art, prior to modification by the teachings herein. Although FIG. 3 depicts a simple balloon structure, it may have any of the features known for such balloons, including surface roughening, texturing, cutting or scoring elements and so on.

An angioplasty balloon of the type depicted schematically in FIG. 3 is often able to open a closed vessel in a very short period of time, for instance in seconds or minutes. Whilst the initial procedure is fast, there is the risk significant risk of further closure of the vessel, for instance by repeated collapse or restenosis. This can be caused by a number of factors including reactive hyperplasia resulting from the vessel opening procedure. Vessel closure can occur again within a few weeks or months of the medical procedure.

In the examples described briefly above in connection with FIGS. 2 and 3, it has been found that the administration of suitable bioactive agents into the vessel wall from the stent and/or from the medical balloon can substantially retard or prevent subsequent closure of the vessel due to restenosis. A variety of bioactive agents suitable for such purposes are known in the art including, for instance, antithrombogenic agents, thrombin inhibitors, tissue plasminogen activators, thrombolytic agents, fibrinolytic agents, vasospasm inhibitors, antiplatelet agents, anti-proliferative agents and so on. A particularly effective bioactive agent known in the art is paclitaxel, others including dexamethasone, Sirolimus (also known as rapamycin), heparin and numerous other agents and compounds. A list of suitable bioactive agents is given at the end of this specification, though it is to be understood that the list is not exhaustive.

The bioactive material is coated onto the medical device, for example the stent 10 of FIG. 1 or the balloon 40 of FIG. 3, so as to be released from the medical device into the tissues of the vessel 24, and should be dispensed at a rate suitable for treating the required medical condition. In the case of a stent or other implantable medical device, it may be desirable for the bioactive material to be released over a prolonged period of time, for example weeks or months. In the case of a medical device which is temporarily deployed in a patient's vessel, such as angioplasty balloon or a device deployment balloon, the bioactive agent must typically be released from the balloon in a very short period of time, for instance within seconds or minutes, although sometimes could be up to an hour or more.

It is important that the bioactive agent is held onto the medical device during deployment of the device in the patient without excessive loss of bioactive material into the patient's bloodstream, for instance. For this purpose, the prior art has suggested restraining the bioactive material, for instance in a containment or time release layer or matrix. Examples include: porous polymer layers into which bioactive material can be embedded, enclosed chambers holding the bioactive material, outer coatings disposed over the bioactive material and which dissolve or open during the deployment process, encapsulation of the bioactive material in capsules or pellets, and so on. Such containment measures can lead to a number of disadvantages, including undesirable delayed administration of the bioactive material into body tissues, presence of a foreign substance in the body, possible onset of stenosis caused by the carrier device, and so on.

The optimal solution is to apply the bioactive agent in the absence of any containment or time release substance and from a layer which is predominantly or entirely made of bioactive agents. In this manner, after administration of the bioactive agent or agents, the medical device remains free of agent delivery substances (polymer layers, for example) and no unnecessary carrier substances are released into the patient's body. The problem, however, has existed with getting a bioactive agent to be held sufficiently well on the medical device.

The inventors have discovered that certain treatments of the medical device, and in particular the surface or surfaces of the device intended to be coated with one or more bioactive agents, can substantially increase the adhesion of the bioactive agent to the medical device before and during deployment of the medical device in the patient. The applicant's co-pending European patent application published as EP-3,192,534 describes the functionalisation of the surface of the medical device to be coated by acidification or basification to increase the adhesive characteristics of the surface and avoid the use other mechanisms to retain the bioactive agent on the device.

It is not always the case that a medical device needs to carry a drug for administration to the patient, even though this is advantageous in many instances.

Whether or not the medical device carries a drug there are, as described in the Background Art section above, two other characteristics relevant to the use of implantable medical devices, whether long term or short term, namely thrombogenesis and endothelialisation. As these effects are described in detail in the Background Art section, this is not repeated here. The preferred embodiments described below provide a structure that can reduce or eliminate thrombogenesis and/or enhance endothelialisation. As is described below, this is by application of a layer or coating of a saturated carboxylic acid to the relevant surface or surfaces of the medical device, which act as a mask hiding the medical device from the body. The medical device can be treated so that all of its exposed surfaces are covered in a saturated carboxylic acid or only some. The coating may be used to carry a drug or other bioactive agent on at least one surface (or part thereof) of the medical device. Examples are set out below.

The coating of a saturated carboxylic acid could be described as functionalisation of the surface or surfaces of the medical device, that is the treatment of the or one or more surfaces of the medical device with a saturated carboxylic acid to cause a change in the surface characteristics of the surface. This coating or functionalisation deposits onto the surface or surfaces saturated carboxylic acid species, which bind to the device surface. They can, when it is desired to carry a bioactive agent on a part of the device, also provide a bonding site for the conjugate base of the bioactive material.

In many cases the saturated carboxylic acid species are deposited as individual molecules. They do not form a polymer matrix, for instance. They are preferably monomeric, not polymeric. As is described in further detail herein, the layer of saturated carboxylic acid is preferably non-porous and consists of at least 90%, preferably 100% of the saturated carboxylic acid or a derivative thereof. The layer is preferably of pure saturated carboxylic acid. It should be understood that there may be trace amounts of other materials in the layer, but these will have no material effect on the characteristics of the saturated carboxylic acid layer.

The coating or functionalisation process preferably does not remove the oxide layer on the contact surface or surfaces, but attaches saturated carboxylic acid components to the oxide layer. The attached saturated carboxylic acid base components could be described as becoming part of the oxide layer. Leaving the oxide intact maintains the stability of the treated surfaces of the medical device while altering the bonding properties of the oxide layer.

As will be apparent from the examples below, significant improvements in thrombogenesis and endothelialisation is experienced by this functionalisation. Better results can be achieved by first cleaning the contact surface or surfaces of the medical device to remove impurities, generally acquired during and after the manufacturing process. This can substantially increase the amount of carbon functional groups on the contact surface(s) of the medical device.

Functionalisation by acidification may be carried out by a relatively strong acid, for instance having a pH of around 1.5, although tests have shown that a large range of acids in a large pH range can be effective also.

The examples described below relate to acidification with citric acid as an example material. A combination of citric acid with another saturated carboxylic acid, such as acrylic acid, is also suitable. In other tests, a combination of citric acid and citrate has been shown to be effective. In practice, use of a saturated carboxylic acid alone is sufficient for providing the desired effects. There are instances, on the other hand, where a particular coating may be desired, for example a thick coating, in which case a combination of a saturated carboxylic acid and its base derivative may be used. For example, incorporation of citrate into a layer of citric acid can help maintain the layer stable in use. Typically, citric acid remains the dominant component of the layer. In such a case, the layer may be made of 50%±20% of the saturated carboxylic acid, for example citric acid, and 50%±20% of its conjugate, for example citrate.

While the examples below focus on citric acid and, as appropriate its conjugate, it is to be understood that these are examples only and that the teachings herein and of the examples are equally applicable to the other saturated carboxylic acids contemplated herein, by substitution.

The specific embodiments described below are directed to a stent formed of nickel titanium alloy (for instance Nitinol) which may be partially coated with paclitaxel, a preferred bioactive agent. The skilled person will appreciate that this is an example only and that the teachings herein are applicable to the other stent materials, including metals, metal alloys and also polymer based stents. The teachings herein are not limited to stents only and can be applied to other medical devices of which examples are given elsewhere.

Figure 4:
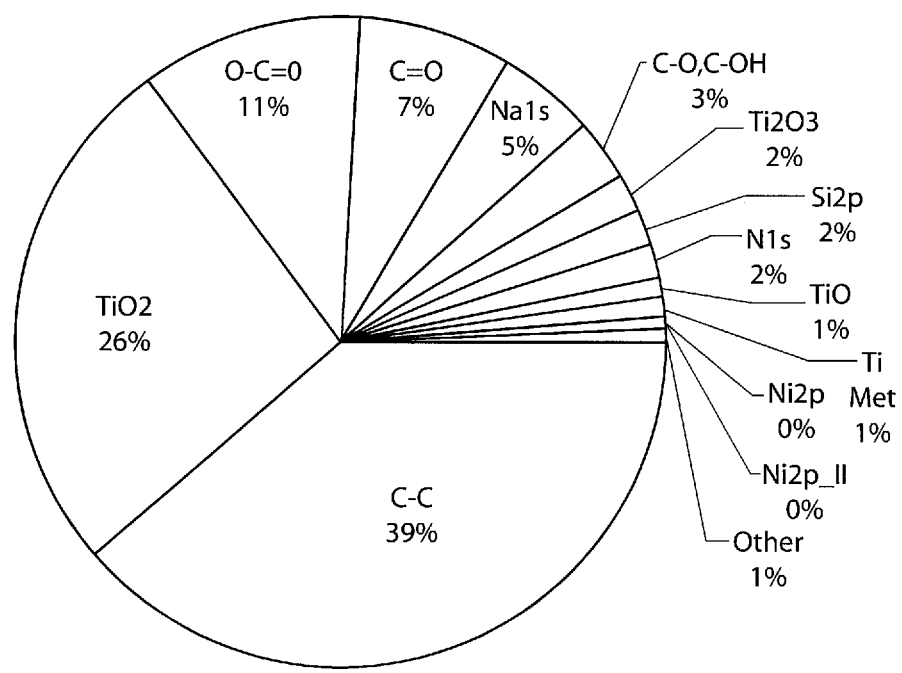
FIG. 4 is a chart depicting the constitution of a cleaned contact surface of a Nitinol stent.

Referring now to FIG. 4, this shows the constitution of a contact surface of a Nitinol stent, measured by x-ray photoelectron spectroscopy (XPS) following functionalisation of the surface with citric acid. As explained above, this functionalisation deposits onto the device surface acidic species which change the adhesive characteristics of the surface. As can be seen from FIG. 4, the treated contact surface exhibits a high percentage of carbon-to-carbon (C—C) components, a high proportion of titanium dioxide and also other components including O—C=O, C=O and other carbon and oxygen components.

Functionalisation by acidification substantially reduces the amount of nickel at the contact surface, which can be advantageous.

Even though it has been found that functionalisation by acidification only provides a notable increase in adhesion of a bioactive agent onto the medical device, it has been found that cleansing of the contact surface or surfaces of the medical device prior to acidification results in even better bioactive material retention on the medical device. This is demonstrated below in connection with FIG. 7.

Figure 5:
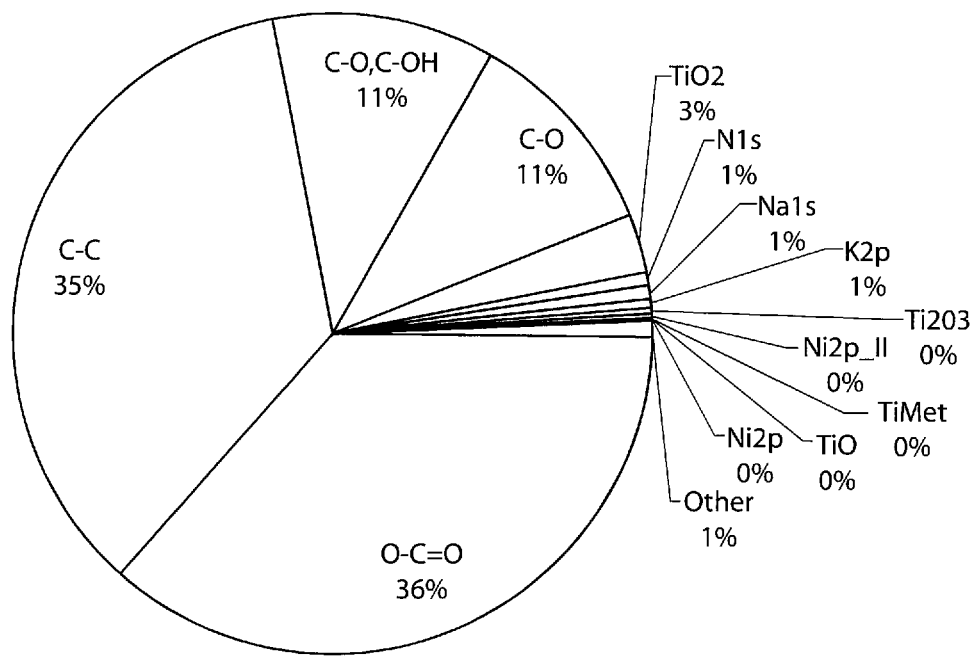
FIG. 5 is a chart depicting the constitution of a contact surface of a Nitinol stent coated with a saturated carboxylic acid layer according to the teachings herein.

Referring first to FIG. 5, this shows the constitution of a contact surface of a Nitinol stent which has been ethanol cleaned then atomically cleaned, for example by means of a plasma, and then acidified, in this example by use of citric acid.

Cleaning with an alcohol such as ethanol, can remove larger impurities from the contact surface. Plasma cleaning provides an atomically cleaned surface, removing in particular carbon components which may have adhered to the contact surface during or after manufacture. The plasma treatment is chosen to be relatively low energy so as not to remove the oxide layer on the outer surface(s) of the medical device.

Example 1—Plasma Cleaning

Suitable plasma machines include the Gatan Solarus Model 950 and Diener Femto type B. An example of an appropriate plasma cleaning treatment, for an $H_2 O_2$ plasma, has the following characteristics:

Frequency: 13.56 MHz

Power Used: 90 W

Pressure: Maintained at 0.4 mbar with water vapour during the run (no other gas required)

Purging: The plasma chamber is gas purged and gas ventilated after the cleaning cycle using nitrogen Cycle Time: 5 minutes Plasma pre-treatment results in the generation of an even greater extent of functionalised carbon bond species at the contact surface of the medical device during the process of acidification, as can be seen in FIG. 5. The amount of titanium dioxide at the contact surface is substantially reduced compared to the case of functionalisation only (FIG. 4). The predominant acidic species of the contact surface are, in this example: O—C=O, C—O, C—OH and C=O. These species provide an acid polar element to the surface energy of the contact surface(s) of the medical device and one which is very stable across the entire extent of the contact surface. This is advantageous not only when the acid layer is the outermost layer but also provides better retention of the bioactive agent to the contact surface.

Example 2—Caustic Cleaning

The inventors has discovered that in place of plasma cleaning, the medical devices can be cleaned by caustic cleaning. In one example, this can be by means of caustic soda, although other caustic cleaning agents may be used in other embodiments.

In this example, the stent were cleaned by the following method:

1) preparation of caustic medium by dissolving 0.1 grams of sodium hydroxide (NaOH) in 100 millilitres of water. The medium had a pH of around 12.5 once stent for coating had been placed into the cleaning medium;

2) leave stent to soak for 30 minutes;
3) rinse the stent in water preferably multiple times (for example ten times) post soaking. After rinsing, the stent was found to have a pH of around 7; and
4) transfer stent directly to coating station without drying.

Example 3—Coating by Spraying

In this example, the stent was coated with a layer of citric acid by the following method:
1) the stent was held vertically in front of a spray gun;
2) the spray gun was positioned with the nozzle aligned with the radial centre of the stent;
3) the stent was rotated three full turns per spray pass;
4the spray gun was operated for a total of 6 passes;
5) depending on the length of the stent and reach of the spray, the spray nozzle also moved along the longitudinal axis of the stent. In this example, the spray gun was moved at a speed of 1500 mm/min along the length of the stent;
6) the spray gun was operated at an atomisation and fan pressure both of 50 PSI;
7) citric acid in solution was dispensed from the spray gun at a rate of 0.25 ml/min;
8) citric acid solution used was: ACS reagent≥99.5%, mix 1 g in 100 ml of water;
9) after coating, the coating was dried.

It is preferred that the coating is dried after every spray pass.

Example 4—Coating by Dipping

In other embodiments, the acid coating may be applied by dipping instead of by spraying.

In this example, the method included the steps of:
1) dipping the stent in a 5% citric acid solution (5 g in 100 mL), pH 1.8, for 2 hours at ~30° C.;
2) after 2 hours of dipping in the citric acid solution, the solution is drained and the stent rinsed 10 times with water. The pH should remain at a stable ~pH 7 after the final rinse;
3) the stent is placed on lint free cloth after rinsing to dry. In another embodiment, the stent is hung to dry.

The skilled person will appreciate that spraying and dipping are just two examples of suitable coating methods and that the teachings herein may use other coating methods including, for instance, rolling and sublimation.

Example 5—Coating with Citric Mixed with Citrate

In another example, a stent was coated with a mixture of citric acid and citrate.

The following method was used:
1) make 1% citric acid solution and 1% calcium citrate solution;
2) mix together in equal volumes. Measure pH, which should be in the region of 3.26. If necessary, alter the proportions of citric acid and calcium citrate as appropriate to achieve a pH in the region of 3.25;
3) coat the stent by spraying or dipping, for instance in accordance with the one of the above Examples.

In all cases, the acid coating is dried, for example in air or by forced drying. This may be carried out between each coating step or at the end of coating.

After coating with the saturated carboxylic acid, the stent (or other medical device) is preferably washed, for example in ethanol. This does not remove the saturated carboxylic acid layer.

It has been found that the optimal amount of saturated carboxylic acid applied on the stent of around 25 micrograms per 10 millimetres of stent length, providing a coating of around 100 nanometres for a 40 millimetre length stent.

For example, 6×40 mm and a 7×40 mm stents having abluminal surface areas of 125.66 mm^2, and lateral surface areas of 407.33 mm^2, have a total surface area of 534.99 mm^2. N.B.: Real surface area variation is ±5%

Assuming the weight of citric acid is 100 micrograms (0.0001 g) and the anhydrous citric acid density is 1.665 g/cm^3 (0.001665 g/mm^3), then the thickness of the citric acid layer is T (mm) as below:

$$0.001665 \text{ (g/mm}^2\times534.99 \text{ mm}^2)\times T \text{ (mm)}=0.0001 \text{ g}$$

So T=112.3 nm

In this case there is 0.1869 μg of citric acid per 1 mm^2 of surface.

If the weight of citric acid is 150 μg, T would equal 112.3*1.5=168.5 nm

It is not necessary for the abluminal and luminal sides of the stent (or other medical device) to have the same thickness of coating. In practice, the luminal side may have a thinner coating and still be effective.

The acid may be applied across the entire surface of the stent, with no gaps, but experiments have established that it is not necessary to have an even coating of acid on the stent surface in all cases. The functionalisation by spraying applies enough acidic component to the contact surface as to provide the stated benefits of enhanced endothelialisation and reduced thrombogenicity, particularly with multiple passes across the surfaces.

Figure 6:
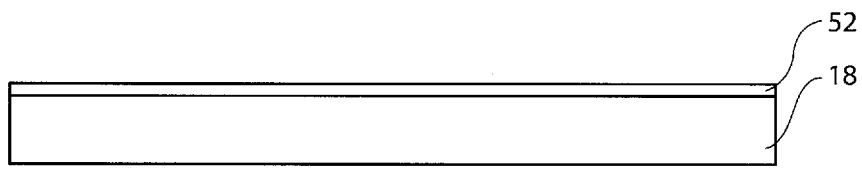
FIG. 6 is a schematic diagram of a transverse cross-sectional view of a stent strut of the stent of FIGS. 1 and 2 to show an abluminal coating on the contact surface.
Figure 7:
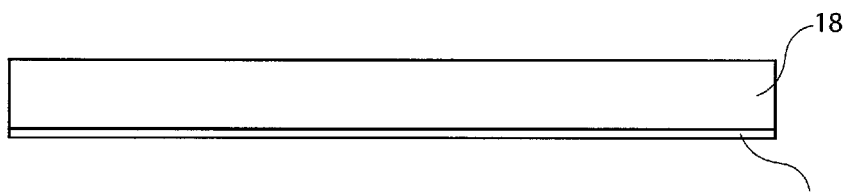
FIG. 7 is a schematic diagram of a transverse cross-sectional view of a stent strut of the stent of FIGS. 1 and 2 to show a luminal coating on the contact surface.
Figure 8:
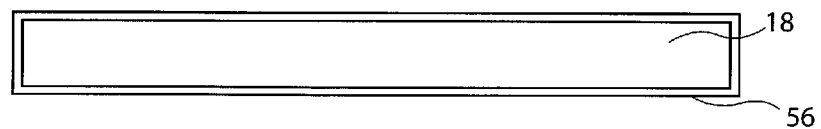
FIG. 8 is a schematic diagram of a transverse cross-sectional view of a stent strut of the stent of FIGS. 1 and 2 to show a coating on all the exposed surfaces of the strut.

Referring now to FIG. 6, there is shown a schematic of view of a strut 18 of stent 10, having a coating or layer 52 of a saturated carboxylic acid on an abluminal surface of the state strut. The characteristics of the preferred embodiment of the layer of saturated carboxylic acid are described in further detail below. In this particular embodiment, the stent 10 is provided with a coating 52 only on the abluminal surfaces and is otherwise free on any other coatings. By contrast, FIG. 7 shows an embodiment of stent strut 18 which is coated on its luminal surface with a layer of saturated carboxylic acid 54. FIG. 8 shows embodiment of strut 18 which is entirely coated with a layer 56 of saturated carboxylic acid. In this embodiment no surface of the strut 18 is left bare and in practice this is representative of all the exposed surfaces of the medical device being coated with a layer of a saturated carboxylic acid.

Figure 9:
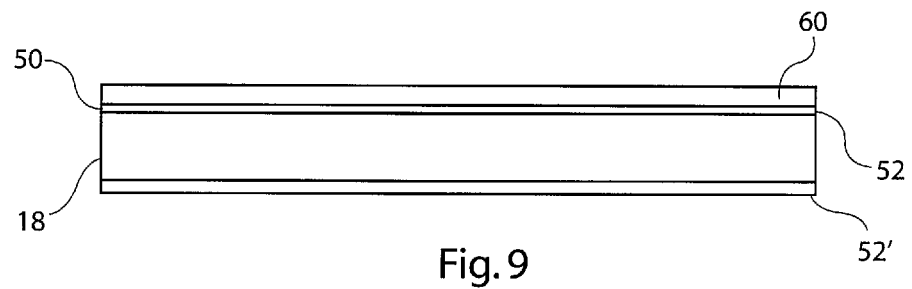
FIG. 9 is a schematic diagram of a transverse cross-sectional view of a stent strut of the stent of FIGS. 1 and 2 to show an abluminal coating on the contact surface and a layer of bioactive material disposed on the coating.

FIG. 9 shows an embodiment in which a stent strut 18 has on its abluminal surface a coating 52 of a saturated carboxylic acid and overlying the latter a layer 60 of a bioactive material. This arrangement is similar to that of the applicant's earlier European patent application number EP-3,192,534, in which a full description of the structure is given. On the other hand, the luminal surface of the strut 18 has a layer of a saturated carboxylic acid that is the outermost layer of that surface of the strut. It will be appreciated, that the strut 18 may be coated on all of its surfaces, with a layer of a bioactive agent only on one of the strut surfaces (in this example the abluminal surfaces).

In the case of coating the abluminal surfaces of the tubular structure 12 of the stent, that is the struts 18 thereof, the bioactive agent 54 is deposited onto the acid treated contact surface 52 (for example by spraying, rolling, dipping, sublimation or the like), without it being necessary to embed the bioactive agent in any containment matrix or layer, as is necessary with the prior art. It is preferred that the bioactive agent layer 60 is distinct from the base support (formed of the structure 14 and saturated carboxylic acid coating 52). Thus, the exposed surface of the bioactive material layer 60 is solely the bioactive material (and possibly any functional groups includes with it, such as excipients and so on). On the other hand, the luminal surfaces of the struts, and as a consequence the stent, will exhibit improved thrombogenic qualities.

While FIG. 9 shows a bioactive coating on the abluminal side of the medical device, for instance to treat the vessel wall tissue, other embodiments may have the bioactive material coating on the luminal side of the device, for instance to treat the vessel fluid. This could, for example, be a blood thinning agent or any other appropriate bioactive agent.

Figures 10, 11:
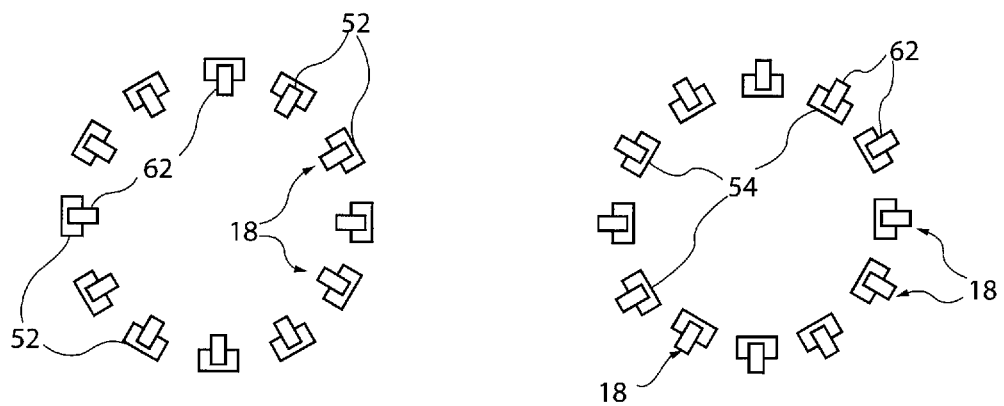
FIGS. 10 and 11 are schematic transverse cross-sectional views of a stent according to FIGS. 1 and 2 showing, respectively, luminal and abluminal coatings on the stent struts.

The arrangements of FIGS. 6 and 7, as they are likely to occur in practice, are shown in FIGS. 10 and 11 respectively. It is to be understood that when reference is made to the stent struts being coated on their abluminal sides, that in the preferred embodiments this means that the stent itself has a coating on all its abluminal surfaces, such that the entire of the stent exhibits the advantages of the coating. Similarly, a luminal coating of the struts 18 will result in the stent overall having a coating on its luminal surfaces. In practice, and as described in further detail below, a coating on one of the luminal and abluminal sides of the stent 10 will typically result in coating material extending at least part way-along the sides 62 of the stent struts 18, in effect providing a depth to the coating, advantageous in being able to accommodate the anatomy of the vessel into which the stent is deployed, for instance to accommodate wall tissue that will press into the interstices between stent struts 18.

The stent can be treated so as to have a saturated carboxylic acid coating in a variety of ways as described herein. In the preferred embodiments, the stent struts may be entirely coated with a saturated carboxylic acid, most preferably citric acid, so as to exhibit improved endothelialisation and reduced thrombogenesis, and also as desired to act to hold a bioactive agent over some of the surfaces of the stent. However, in some cases it may be desired to have the coating of saturated carboxylic acid on only some of the surfaces of the stent.

Figure 12:
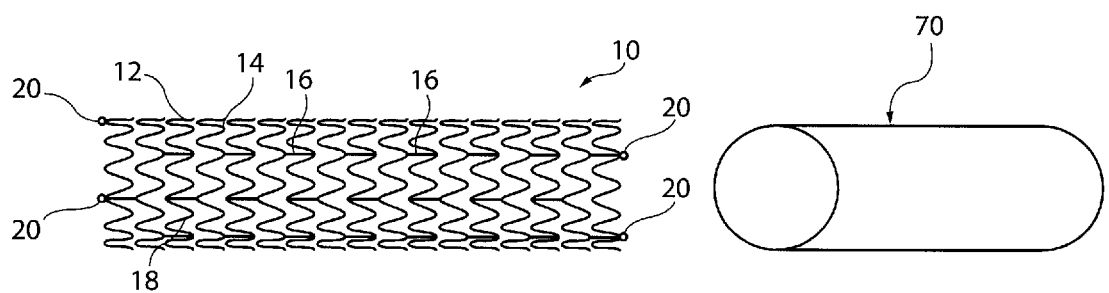
FIGS. 12 and 13 are schematic views of a stent according to FIGS. 1 and 2 and mandrels for use in coating the luminal and abluminal surfaces of the stent.

FIG. 12 shows an example of arrangement for coating the abluminal surface of a stent 10. The arrangement includes a mandrel 70 designed to fit inside the stent 10, such that the stent 10 fits securely onto the mandrel 70.

The stent 10 may be crimped onto the mandrel 70 as desired. A coating of a saturated carboxylic acid can then be applied to the abluminal surfaces of the struts 18 of the stent 10, for example by spraying, dipping, rolling, sublimation and so on. In cases where the stent 10 is crimped onto the mandrel 70, there may be no gaps between the stent struts 18, in which case only the abluminal (external) surfaces of the struts 18 will be coated. On the other hand, where there are interstitial gaps between the struts 18, at least a part of the side surfaces 62 of the struts 18 will be likewise coated, depending upon the coating method and to what extent the stent 10 embeds into the surface of the mandrel 70.

Figure 13:
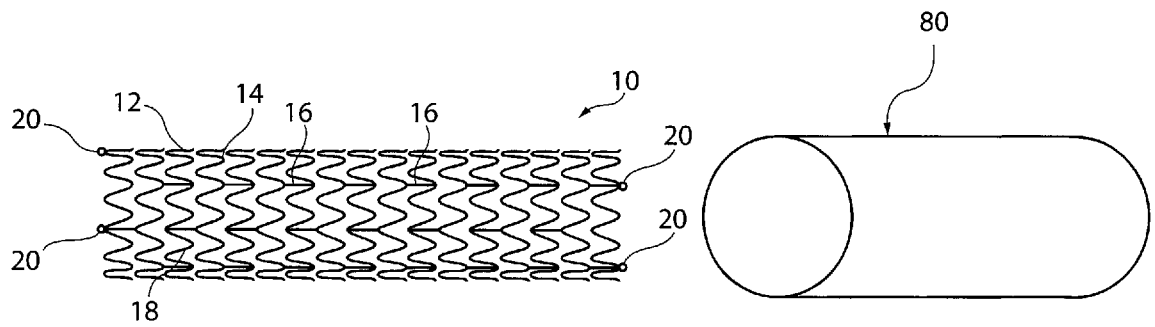

FIG. 13 shows another example arrangement provided with a sleeve 80 into which the stent 10 can be disposed, with the abluminal surface of the stent in abutment with the inner surface of the sleeve. The reader will appreciate that this arrangement is suitable for coating the luminal (inner) surfaces of a stent 10, and may have characteristics similar to the arrangement of FIG. 12.

The reader will appreciate that FIGS. 12 and 13 are schematic and simplistic examples of arrangements to illustrate ways to coat selective surfaces of a stent and that details of the apparatus and other apparatus will be well within the skillset of the person skilled in the art.

Tests have also established that a concentration of 1% saturated carboxylic acid is optimal (and preferably citric acid), although concentrations from 0.1% to 10% have also been found to work. This may be applied in a plurality of spray passes, typically from around 5 to 20 passes, most preferably from around 10 to 20 passes. A greater concentration of acid or a greater number of passes can result in an excessive amount of acid molecules being deposited onto the stent surface, which is not desired.

Figure 14:
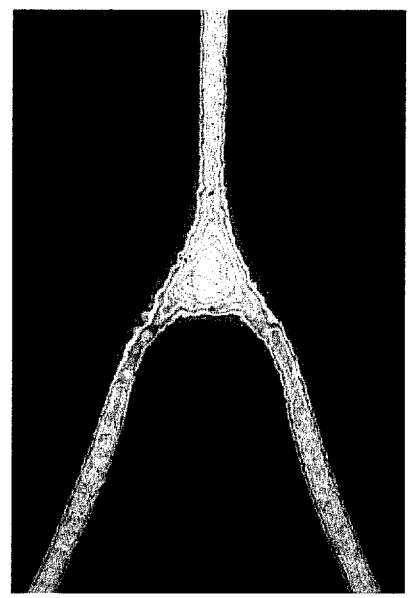
FIGS. 14 to 17 are photographs of parts of a Nitinol stent having the shown surfaces treated according to the teachings herein.
Figure 15:
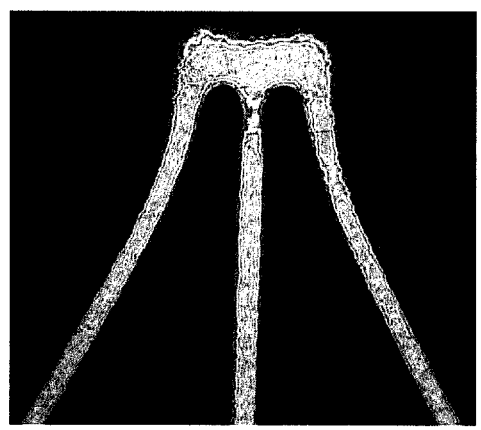

Referring to FIGS. 14 and 15, these are photographs of citric acid coated surfaces of Nitinol stents under polarised light, in which the citric acid has been deposited by spraying in a manner as taught herein and consistent with Example 3. In the example shown, the stent was plasma cleaned prior to coating. It may not always be necessary for the acid molecules to cover the entirety of the treated stent surfaces, and it has been found that even a partial covering can provide a good coating. A covering of 80% of saturated carboxylic acid has been found to be effective, and up to and including total (100%) coverage. In the particular example shown, the citric acid was coated as a solution of 1.0 g of citric acid in 100 ml of water in multiple spray passes.

Figure 16:
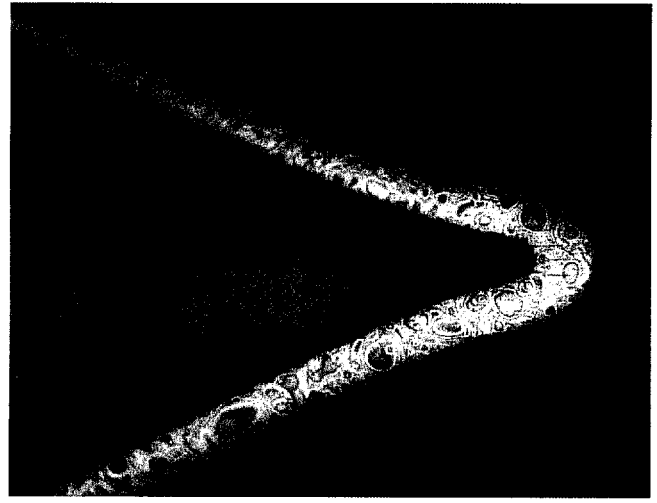
Figure 17:
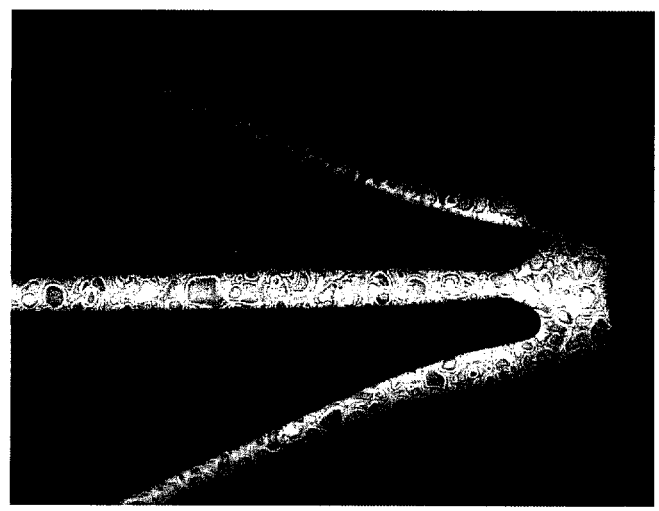

FIGS. 16 and 17 show a similar stent, which is this embodiment has been coated with a mixture of citric acid and citrate, specifically a mix of 0.6 g citric acid and 0.4 g calcium citrate in 100 ml water and coated by spraying in multiple passes.

In both cases, it can be seen that the coating or layer extends uniformly across the surface of the stent and in practice is stable and well adhered to the base structure of the stent. It has been found that the layer or coating does not fall off during prolonged use.

Figure 18:
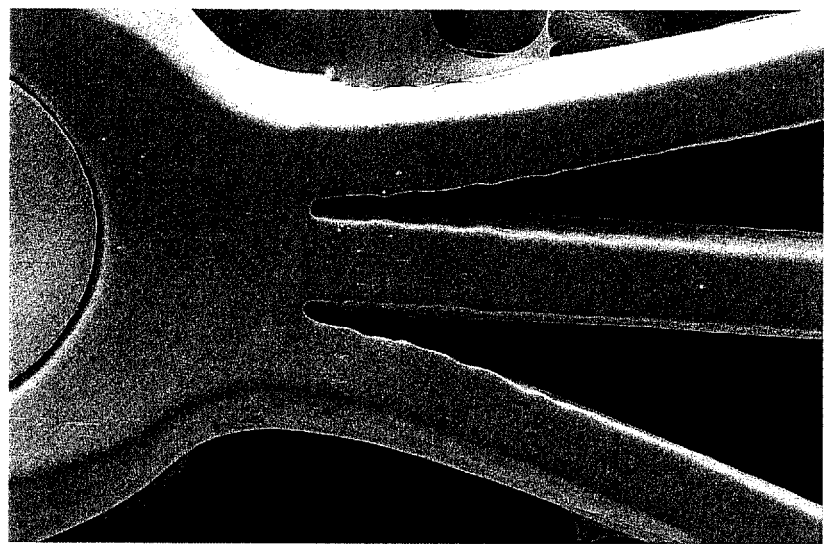
FIGS. 18 and 19 are enlarged photographic views showing sections of a citric acid coated stent surface according to the teachings herein after being subjected to porcine blood for 30 minutes.
Figure 19:
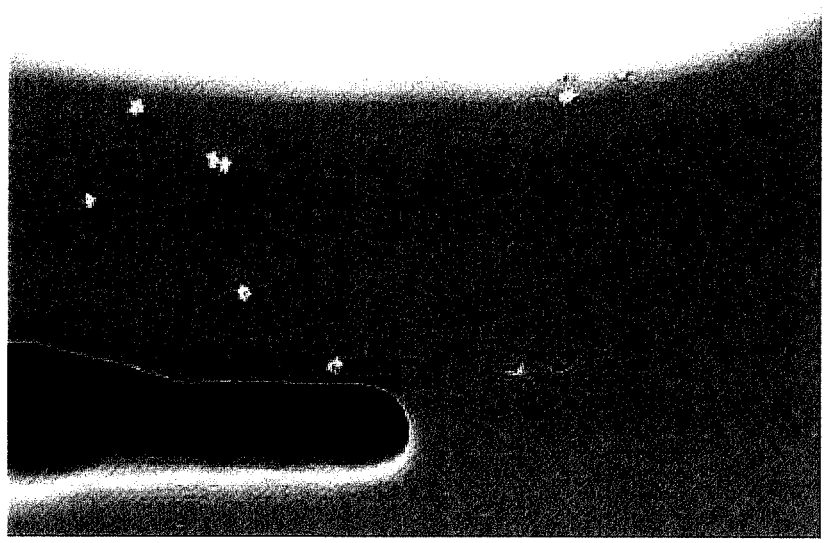
Figure 20:
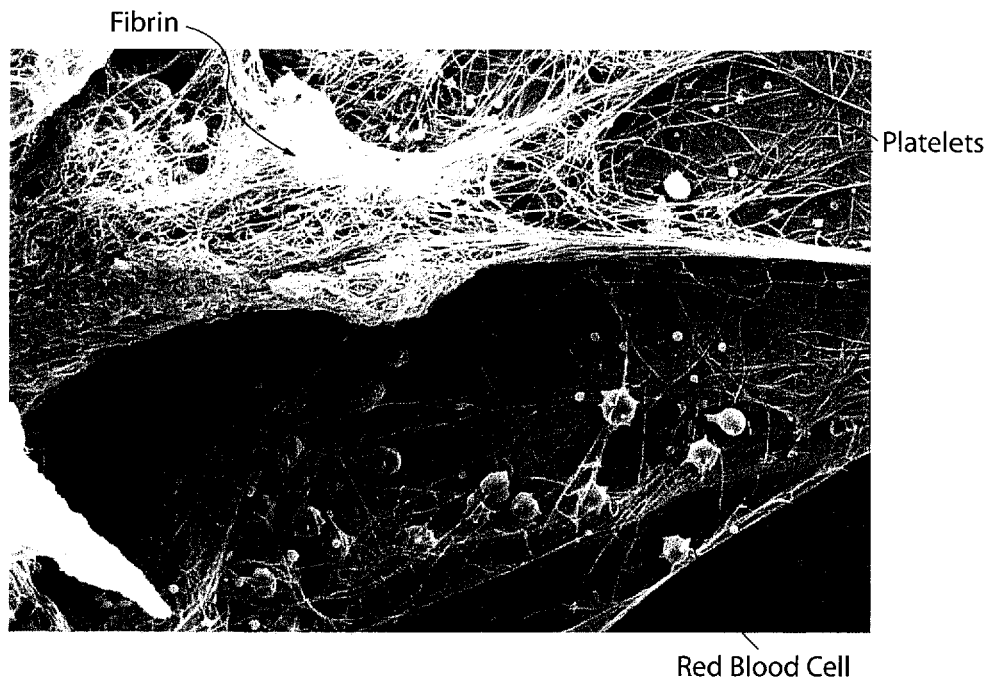
FIGS. 20 and 21 are enlarged photographic views showing sections of, respectively, an EtO sterilised control stent and an ethanol cleaned stent after being subjected to porcine blood for 30 minutes.
Figure 21:
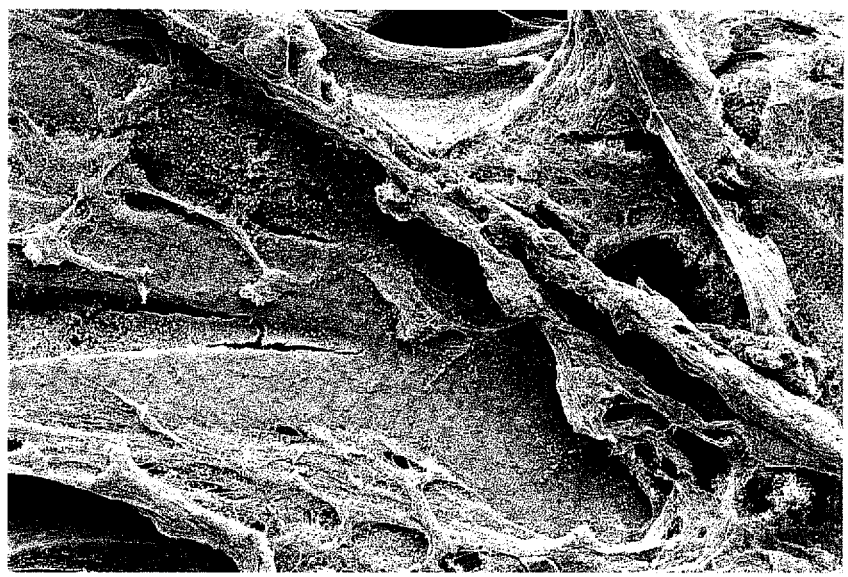

FIGS. 18 and 19 show a stent treated in accordance with the teachings herein after placement in a simulated vessel and subjected to porcine blood under pulsatile flow for a period of 30 minutes. As can be seen in these Figures, the stent has virtually no deposits of platelets, blood cells or fibrin. This is in marked contrast with conventional stents, of which examples can be seen in the photographs of FIGS. 20 and 21, which show, respectively, an ethylene oxide (EtO) sterilised control stent and an ethanol washed stent having been likewise exposed to porcine blood as the stent of FIGS. 18 and 19. In all cases the stent was the same save for the acidification of the stent in the embodiment of FIGS. 18 and 19. The control stent shown in FIG. 20 had significant deposits of fibrin, platelets and red blood cells, which would contribute to the generation of thrombi on the stent and re-narrowing of the vessel. The situation is very similar with the ethanol washed stent, demonstrating the efficacy of acid coated stents (and other medical devices).

In practice, the inventors have discovered that whichever way the acid (or derivative) is applied to the stent, by spraying or dipping for example, there will be significantly reduced attachment of platelets on the treated surfaces, as well as of red and white blood cells and fibrin. With both methods there is a significant reduction in the amount of fibrin that attaches to the stent, in the case of spray coated stents any fibrin being loosely attached.

These results have been observed both with coatings of citric acid only as well as with coatings being a mixture of citric acid and citrate. These findings extend to combinations of citric acid with other saturated carboxylic acids too.

Figure 22:
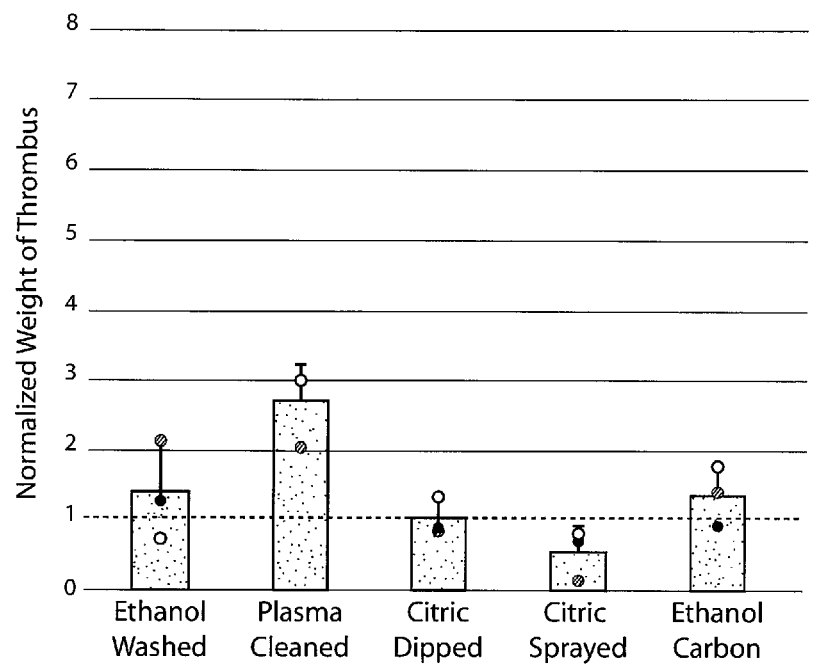
FIG. 22 is a chart showing the normalized weight of thrombus formation of a variety of stent structures including structures modified as taught herein.

With reference now to FIG. 22, this is a bar chart showing the normalized weight of thrombus formations of an exemplary stent after exposure to porcine blood for 30 minutes.

As can be seen, the stents that had exposed or outer layers of citric acid, whether sprayed or dipped, exhibited substantially lower weight of thrombus formations compared to stents that were ethanol washed or plasma cleaned.

Figure 23:
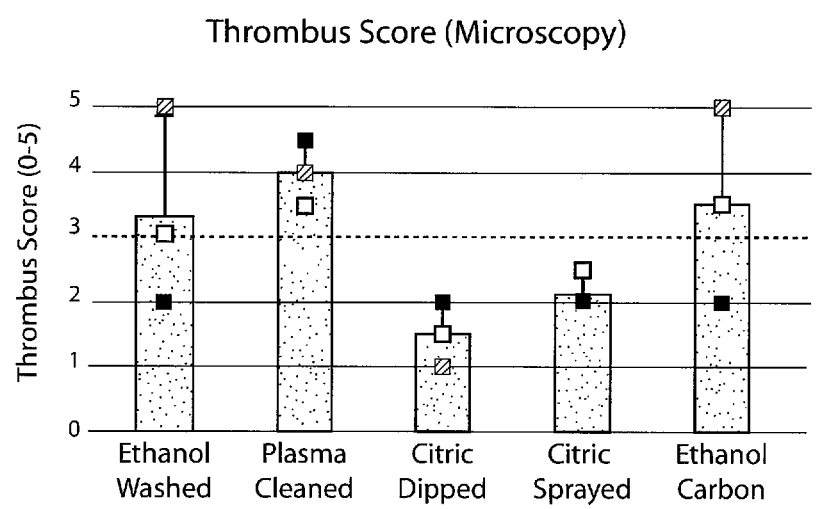
FIG. 23 is a chart showing the extent of thrombus formation of a variety of stent structures including structures modified as taught herein.

With reference to FIG. 23, the bar graph shown depicts the nature of the thrombus formations on the stent. The scores in the bar graph are representative of the following:

0=no significant thrombus
1=minimal thrombus formations (in one or two places)
2=minimal thrombus formations covering less than 25% of the stent
3=moderate thrombus formations covering 26-50% of the stent
4=moderate to high thrombus formations covering 51-75% of the stent
5=significant thrombus formations covering more than 75% of the stent.

As can be seen, the citric acid coated stents exhibited significantly less thrombus formation than conventional stents. The same applies to stents having a covering of citric acid and citrate.

The difference between the citric acid dipped stent and the citric acid sprayed stent is believed to be caused the dipping process used being less efficient than the spraying process. However, by adjustment of the dipping process, for instance to increase dipping time, concentration of citric acid, number of dipping cycles and so on can improve the quality of the coating on the stent and as a result improve hemocompatibility further.

It is believed that citric acid is a particularly good coating material given that citric acid is prevalent in the body, typically at amounts of around 2.7 kg in an adult. As a result, it is believed that the citric acid coating on a medical device hides the medical device from the body and prevents it from being seen as a foreign object. It is believed that the citric acid coating is seen as a biomimetic citric acid member.

The enhancement in terms of endothelialisation is equally marked by the provision of a saturated carboxylic acid, preferably citric acid, layer, probably due to the fact that the vessel wall cells do not perceive the acid coating as a foreign object, thereby allowing endothelialisation. The skilled person will also recognise that thrombus deposits on a medical device will adversely affect the progress of endothelialisation.

While the embodiments described above dissolve citric acid in water, it could equally be dissolved in ethanol. Use of ethanol is particularly useful for application to a hydrophobic base structure, such as a polymer implantable medical device or medical balloon, catheter and so on.

It is preferred that the saturated carboxylic acid is applied at a low concentration, as indicated above. However, it may be desirable in some cases to apply the acid at higher concentrations or acidities, which may increase the amount of acid that is applied to the treated surfaces. In such a case, as well as in all other embodiments, there may be provided a interstitial layer between the base structure of the medical device and the layer of saturated carboxylic acid, which can act as a protective and/or binding element. A suitable material for such a layer is heparin.

Although the method and system described above and in conjunction with coating of a stent, the same method and system can be used to coat many other medical devices. Examples include stent grafts, vascular filters, vascular plugs or occluders, prosthetic devices such as prosthetic valves, as well as medical devices only temporarily implanted into a patient including, for example, medical balloons, catheters, cannulae, wire guides, other elements of introducer assemblies and diagnostic tools.

A filter having its filtration struts treated with a coating as taught herein can reduce the thrombogenic characteristics of the filter, thereby enhancing its performance.

A coating of saturated carboxylic acid or a derivative thereof on the outside surfaces of a medical device, for instance a catheter or wire guide, can be advantageous not only in terms of reducing or avoiding the possibility of thrombus formation on the medical device, but the coating is also very hydrophilic, that is provides a slippery outer surface to the device. This can be particularly advantageous in assisting the trackability of wire guides and catheters in the vasculature of a patient.

In some cases, the citric acid (or other saturated carboxylic acid or derivative thereof) may be impregnated into an element of the medical device, such as the graft material of a stent graft, or may be incorporated into the material of an element of the medical device, for example blended into a polymer bulk compound of at least a part of the medical device.

There has been described a medical device that is at least partially coated with a layer of a saturated carboxylic acid or a derivative or a saturated carboxylic acid in order to enhance biocompatibility, reduce thrombogenesis and enhance endothelialisation. The coating is preferably of citric acid in non-crosslinked form and preferably non-porous so as to mask the underlying structure of the medical device. The acid or base coating forms an outer (outermost) surface of at least a part of the medical device, that is has no other layer or material overlying it, save for in some embodiments a partial coating of a bioactive material. The bioactive material may be on an abluminal side of the device but equally on a luminal side of the device.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The disclosures in the abstract accompanying this application is incorporated herein by reference.

What is claimed is:

1. A medical device including:
a structure for implantation or disposition inside a patient and configured to remain as a permanent implant in the patient, the structure including a luminal surface and abluminal surface, the structure made of a metal or metal alloy, and each of said luminal surface and said abluminal surface presenting an oxide of the metal or metal alloy;
a layer of a saturated carboxylic acid directly on the oxide, the saturated carboxylic acid being non-polymeric and being in non-crosslinked form, wherein said layer of the saturated carboxylic acid is free from polymer matrix material; and
wherein said layer of the saturated carboxylic acid has an abluminal portion at least partially covering the abluminal surface of the structure and a luminal portion at least partially covering the luminal surface of the structure;
said abluminal portion of said layer of the saturated carboxylic acid underlying a layer comprising a bioactive agent, wherein said layer comprising a bioactive agent is free from polymer matrix material;

said luminal portion of said layer of the saturated carboxylic acid being an outermost layer over said luminal surface of the structure; and said abluminal portion and said luminal portion each having a thickness in the range of 10 nanometers to 200 nanometers.

2. A medical device according to claim 1, wherein said layer of the saturated carboxylic acid is at least 90% saturated carboxylic acid or saturated carboxylic acid mixed with a derivative thereof.

3. A medical device according to claim 2, wherein said layer of the saturated carboxylic acid is at least one of:
   a) a layer of citric acid; and
   b) a layer of citric acid mixed with citrate.

4. A medical device according to claim 2, wherein said layer of the saturated carboxylic acid is formed of amorphous saturated carboxylic acid or amorphous saturated carboxylic acid mixed with a derivative thereof.

5. A medical device according to claim 1, wherein said layer of the saturated carboxylic acid is at least one of:
   a) a non-porous layer; and
   b) carrier free.

6. A medical device according to claim 1, wherein said layer of the saturated carboxylic acid consists of a saturated carboxylic acid or a saturated carboxylic acid mixed with a derivative thereof.

7. A medical device according to claim 6, wherein said layer of the saturated carboxylic acid has a thickness of less than 100 nanometres.

8. A medical device according to claim 6, wherein the structure is a stent made of a nickel titanium alloy.

9. A medical device according to claim 1, wherein said luminal portion of said layer of the saturated carboxylic acid covers at least 80% of the luminal surface.

10. A medical device according to claim 1, wherein the bioactive agent is paclitaxel.

11. A medical device according to claim 1, wherein the bioactive agent is an antithrombogenic agent.

12. A medical device according to claim 1, wherein the bioactive agent is a thrombin inhibitor.

13. A medical device according to claim 1, wherein the bioactive agent is a thrombolytic agent.

14. A medical device according to claim 1, wherein the bioactive agent is a fibrinolytic agent.

15. A medical device according to claim 1, wherein the bioactive agent is an antiplatelet agent.

16. A medical device according to claim 1 wherein said luminal portion of said layer of the saturated carboxylic acid is effective to enhance endothelialization and/or reduce thrombogenicity of the structure when implanted or disposed inside a vessel of the patient.

17. A medical device, comprising:
a structure for implantation or disposition inside a vessel of a patient and configured to remain as a permanent implant in the patient, the structure being a metal or metal alloy stent and including an abluminal surface for contacting a wall of the vessel and a luminal surface opposite the abluminal surface;
a layer comprised of citric acid, wherein said layer comprised of citric acid is free from polymer matrix material;
wherein said layer comprised of citric acid has an abluminal portion at least partially covering the abluminal surface of the structure and a luminal portion at least partially covering the luminal surface of the structure;
said luminal portion of said layer comprised of citric acid being an outermost layer of the structure over the luminal surface and being effective to enhance endothelialization and/or reduce thrombogenicity of the structure when implanted or disposed inside the vessel; and
a bioactive agent layer positioned over said abluminal portion of said layer comprised of citric acid, wherein the bioactive agent layer includes an anti-proliferative agent, wherein said bioactive agent layer is free from polymer matrix material.

18. A medical device according to claim 17, wherein said layer comprised of citric acid is constituted at least 90% of citric acid or a mixture of citric acid with a citrate salt.

19. A medical device, comprising:
a structure for implantation or disposition inside a vessel of a patient and configured to remain as a permanent implant in the patient, the structure being a metal or metal alloy stent and including an abluminal surface for contacting a wall of the vessel and a luminal surface opposite the abluminal surface;
a layer comprised of citric acid, wherein said layer comprised of citric acid is free from polymer matrix material;
wherein said layer comprised of citric acid has an abluminal portion at least partially covering the abluminal surface of the structure and a luminal portion at least partially covering the luminal surface of the structure;
said luminal portion of said layer comprised of citric acid being an outermost layer of the structure over the luminal surface and being effective to enhance endothelialization and/or reduce thrombogenicity of the structure when implanted or disposed inside the vessel; and
a bioactive agent layer positioned over said abluminal portion of said layer comprised of citric acid, wherein said bioactive agent layer includes paclitaxel or sirolimus, and wherein said bioactive agent layer is free from polymer matrix material.

* * * * *